US008617221B2

(12) United States Patent
Wang et al.

(10) Patent No.: US 8,617,221 B2
(45) Date of Patent: Dec. 31, 2013

(54) APPARATUS AND METHODS FOR BONE FRACTURE FIXATION

(75) Inventors: Robert C. Wang, Las Vegas, NV (US); Mohamed B. Trabia, Las Vegas, NV (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 208 days.

(21) Appl. No.: 13/110,843

(22) Filed: May 18, 2011

(65) Prior Publication Data
US 2011/0218535 A1    Sep. 8, 2011

Related U.S. Application Data

(60) Division of application No. 11/439,611, filed on May 24, 2006, now abandoned, which is a continuation-in-part of application No. 10/293,732, filed on Nov. 12, 2002, now Pat. No. 7,235,077.

(60) Provisional application No. 60/350,785, filed on Nov. 9, 2001.

(51) Int. Cl.
*A61B 17/80* (2006.01)

(52) U.S. Cl.
USPC .......................................................... 606/280

(58) Field of Classification Search
USPC ...................... 606/70–71, 280–281, 902–906
See application file for complete search history.

(56) References Cited

U.S. PATENT DOCUMENTS

| 3,203,098 A | 8/1965 | Petraitis |
| 3,831,608 A | 8/1974 | Kletschka et al. |
| 3,983,878 A | 10/1976 | Kawchitch |
| 4,583,541 A | 4/1986 | Barry |
| 4,889,110 A | 12/1989 | Galline et al. |
| 4,905,679 A | 3/1990 | Morgan |
| 4,966,599 A | 10/1990 | Pollock |

(Continued)

FOREIGN PATENT DOCUMENTS

EP    291632    11/1988

OTHER PUBLICATIONS

Champy, Maxime et al., "Mandibular Osteosynthesis by Miniature Screwed Plates Via a Buccal Approach," *J. Max-Fac Surg.* 6:14-21, 1978.

(Continued)

*Primary Examiner* — Sameh Boles
(74) *Attorney, Agent, or Firm* — Ryan A. Heck; UNR-DRI Technology Transfer Office

(57) ABSTRACT

Apparatus and methods to facilitate fixation of a fracture are disclosed. These apparatus include a bone plate for the fixation of a fractured bone having a plurality of fastener openings so that the bone plate may be secured by a plurality of fasteners across a reduced fracture to fixate a reduced fracture. The bone plate is configured to flex in situ to conform to the surface of the bone while providing sufficient stiffness in the plane of the device to resist forces and moments in the plane. Methods of use of the present invention include fastening the bone plate to a first side of the fracture, flexing portions of the bone plate to bias against the bone surface on the second side of the fracture, fastening the portions of the bone plate so biased to the second side of the fracture, thereby fixating the fracture by fastening the bone plate to the second side of the fracture.

4 Claims, 9 Drawing Sheets

(56) References Cited

U.S. PATENT DOCUMENTS

| | | | |
|---|---|---|---|
| 5,108,397 | A | 4/1992 | White |
| 5,290,281 | A | 3/1994 | Tschakaloff |
| 5,324,291 | A | 6/1994 | Ries et al. |
| 5,330,476 | A | 7/1994 | Hiot et al. |
| 5,634,926 | A | 6/1997 | Jobe |
| 5,704,936 | A | 1/1998 | Mazel |
| 5,766,176 | A | 6/1998 | Duncan |
| 5,807,382 | A | 9/1998 | Chin |
| 5,855,580 | A | 1/1999 | Kreidler et al. |
| 5,947,970 | A | 9/1999 | Schmelzeisen et al. |
| 5,989,256 | A | 11/1999 | Kuslich et al. |
| 5,993,448 | A | 11/1999 | Remmler |
| 6,004,353 | A | 12/1999 | Masini |
| 6,060,641 | A | 5/2000 | Manolidis |
| 6,093,201 | A | 7/2000 | Cooper et al. |
| 6,248,106 | B1 | 6/2001 | Ferree |
| 6,258,091 | B1 | 7/2001 | Sevrain et al. |
| 6,277,124 | B1 | 8/2001 | Haag |
| 6,302,884 | B1 | 10/2001 | Wellisz et al. |
| 6,368,326 | B1 | 4/2002 | Dakin et al. |
| 6,423,068 | B1 | 7/2002 | Reisberg et al. |
| 6,423,069 | B1 | 7/2002 | Sellers |
| 6,575,741 | B2 | 6/2003 | Campbell |
| 6,692,498 | B1 | 2/2004 | Niiranen et al. |

OTHER PUBLICATIONS

Haug, RH et al., "A Biomechanical Evaluation of Mandibular Angle Fracture Plating Techniques," *Journal of Maxillofac Surg.* Oct. 2001, 2 pages, www.ncbi.nlm.nih.gov.

Kroon, Frans H.M. et al., "The Use of Miniplates in Mandibular Fractures," *J. Cranio-Max.-Fac. Surg.* 19:199-204, 1991.

Shetty, Vivak et al., "Fracture Line Stability as a Funtion of the Internal Fixation System: As in Vitro Comparison Using a Mandibule Angle Fracture Model," *Journal of Maxilofac Surg.* 53:791-801, 1995.

Tate, Gregory S. et al., "Bite Forces in Patients Treated for Mandibular Angle Fractures," *J Oral Maxillofac Surg.* 52:734-736, 1994.

Trabia, Mohamed S. et al., "Design of a V-plate-Wire Mandibular Fixation System," *ASME International Mechanical Engineering Congress and Exposition* 2 pages, Nov. 11-16, 2001, NY, NY.

Trabia, Mohamed S. et al., "Design of a V-Plate-Wire Fixation System for a Mandibles," *Advances in Bioengineering* 51:2 pages, 2001.

Wang, Robert C. et al., "A Simple, Effective Means of Mandibular Fixation," *Archotolaryngol Head Neck Surg.* 124:448-452, Apr. 1998.

Wang, Robert C. et al., "The Tension Wire Method—A Simple Effective Means of Mandibular Fixation," *Archtolaryngol Head Neck Surg.* 124:448-452, 1996.

Non-Final Office Action dated Oct. 7, 2009, from corresponding U.S. Appl. No. 11/699,866.

Response to Oct. 7, 2009, Office Action from corresponding U.S. Appl. No. 11/699,866.

Non-Final Office Action dated Jun. 25, 2010, from corresponding U.S. Appl. No. 11/699,866.

Response to Jun. 25, 2010, Office Action from corresponding U.S. Appl. No. 11/699,866.

Final Office Action dated Dec. 28, 2010, from corresponding U.S. Appl. No. 11/699,866.

Amendment and Response to Dec. 28, 2010, Final Office Action from corresponding U.S. Appl. No. 11/699,866.

Non-Final Office Action dated Apr. 24, 2006, from U.S. Appl. No. 10/293,732 (now U.S. Patent No. 7,235,077).

Response to Apr. 24, 2006 Non-Final Office Action filed Oct. 24, 2006, from U.S. Appl. No. 10/293,732 (now U.S. Patent No. 7,235,077).

Response to Nov. 9, 2006 Non-Compliant Amendment filed Dec. 8, 2006, from U.S. Appl. No. 10/293,732 (now U.S. Patent No. 7,235,077).

Non-Final Office Action dated Jul. 25, 2008, from U.S. Appl. No. 11/439,601 (now U.S. Patent No. 7,578,835).

Response to Jul. 25, 2008 Non-Final Office Action filed Dec. 23, 2008, from U.S. Appl. 11/439,601 (now U.S. Patent No. 7,578,835).

Final Office Action dated Mar. 17, 2009, from U.S. Appl. No. 11/439,601 (now U.S. Patent No. 7,578,835).

Response to Mar. 17, 2009 Final Office Action filed Mar. 18, 2009, from U.S. Appl. No. 11/439,601 (now U.S. Patent No. 7,578,835).

Lawson, Final Office Action in U.S. Appl. No. 11/699,866 (Sep. 20, 2013).

APPARATUS AND METHODS FOR BONE FRACTURE FIXATION

CROSS REFERENCE TO RELATED APPLICATIONS

This present utility patent application is a divisional application of, and incorporates by reference, U.S. patent application Ser. No. 11/439,611, filed May 24, 2006, now abandoned which application in turn is a continuation-in-part application of U.S. patent application Ser. No. 10/293,732 filed on Nov. 12, 2002, now U.S. Pat. No. 7,235,077, that, in turn, claims the priority and benefits of U.S. Provisional Application 60/350,785 filed Nov. 9, 2001. The entireties of U.S. patent application Ser. No. 10/293,732 and of U.S. Provisional Application 60/350,785 are incorporated herein by reference. A co-pending application filed on the same date, U.S. patent application Ser. No. 11/439,601, entitled "APPARATUS AND METHODS FOR BONE FRACTURE REDUCTION AND FIXATION," is also incorporated herein in its entirety by reference.

BACKGROUND OF THE INVENTION

1. Field of the Invention

The present invention relates to medical devices and, more particularly, to apparatus and methods for the reduction and fixation of fractures.

2. Description of the Related Art

When a fracture is repaired, the bone fragments are placed in appropriate alignment in an anatomically correct position (reduction). Following reduction of the fracture, the fracture is then fixated, meaning that the bone fragments are prevented from moving from the reduced placement during the healing process. Various apparatus such as bone plates, bone screws, and rods are used for fixation of bone fragments. Following fixation, the fracture is then allowed to heal. After the fracture has healed, the fixation apparatus may be removed or may be left permanently in the body.

Bone plates, which are typically thin and have a plurality of fastener openings for fastening by various fasteners such as bone screws to the bone surface, are often used in cranial and maxillofacial surgery. For example, the repair of mandibular fractures often involves reduction and fixation by various bone plate systems. The surgeon holds the bone fragments in reduction and then applies a bone plate or bone plate system to the bone surface of the bone fragments to fixate the fracture. Often one or more assistants must hold the bone fragments in reduction while the surgeon fixates the fracture by fastening the bone plate or bone plate system. The bone plate may provide sufficient structural support across the fracture so that, when a bone plate or bone plate system is used to fixate a mandibular fracture, the patient may be able to resume some normal eating requiring mastication following the surgery.

Bones, especially in the maxillofacilial region, may have curved or irregular surfaces. The bone plate must be shaped to fit the bone in the region of the fracture prior to attachment. The shaping and fitting process, which generally involves trial and error, is often conducted in the operating theater by the surgeons, and can be time consuming, thereby lengthening the time the patient spends under anesthesia. Sometimes, in order to reduce the patient's time in surgery, the surgeon may shape the bone plate by bending the bone plate to conform to a cadaver specimen prior to conducting the surgical procedure. The hope is that the shape of the bone in the cadaver specimen will approximate the shape of the corresponding fractured bone in the patient, so that only minor adjustments to the shape of the bone plate will be required during surgery and the duration of the surgery will be lessened. This approach is not always satisfactory.

Thus, it is seen that currently available apparatus for fracture fixation have a variety of shortcomings. Therefore, a need exists for an apparatus that gives the support to the fracture of a bone plate and that has the ability to fixate the range of fractures that may be fixated by a bone plate, while being readily conformable to an irregular or curved bone surface.

SUMMARY OF THE INVENTION

Apparatus and methods in accordance with the present invention may resolve one or more of the needs and shortcomings discussed above and will provide additional improvements and advantages as will be recognized by those skilled in the art upon review of the present disclosure.

This present invention provides an apparatus and methods for the fixation of a bone fracture. The apparatus according to the present invention includes a bone plate. The bone plate has a first surface, which may be placed distal to a bone surface and may be configured to be biased against the bone surface. The bone plate has a second surface, which may be placed proximal to the bone surface. The second surface may be designed to be atraumatic to surrounding tissues. A plurality of fastener openings may be disposed between the first surface and the second surface so that the bone plate may be secured to the bone surface by a plurality of fasteners. A plane and a perpendicular to the plane may be defined by the bone plate plus a thickness. The thickness of the bone plate is defined as the distance between the first surface and the second surface along the perpendicular. The bone plate is configured with thin regions to provide flexibility in the direction perpendicular to the plane so that the bone plate may flex generally perpendicular to conform to a bone surface while in situ. The bone plate is configured to have stiffness in the plane sufficient to fixate the fracture by maintaining the fracture in a state of repose.

An apparatus according to the present invention may be used by securing the bone plate to a first fracture side. The method proceeds by flexing the bone plate in situ in the direction perpendicular to the plane such that a first surface is biased against a bone surface on a second fracture side. The fracture is fixated by securing the bone plate to the bone surface on the second fracture side.

Other features and advantages of the invention will become apparent from the following detailed description, and from the claims.

Figure 1:
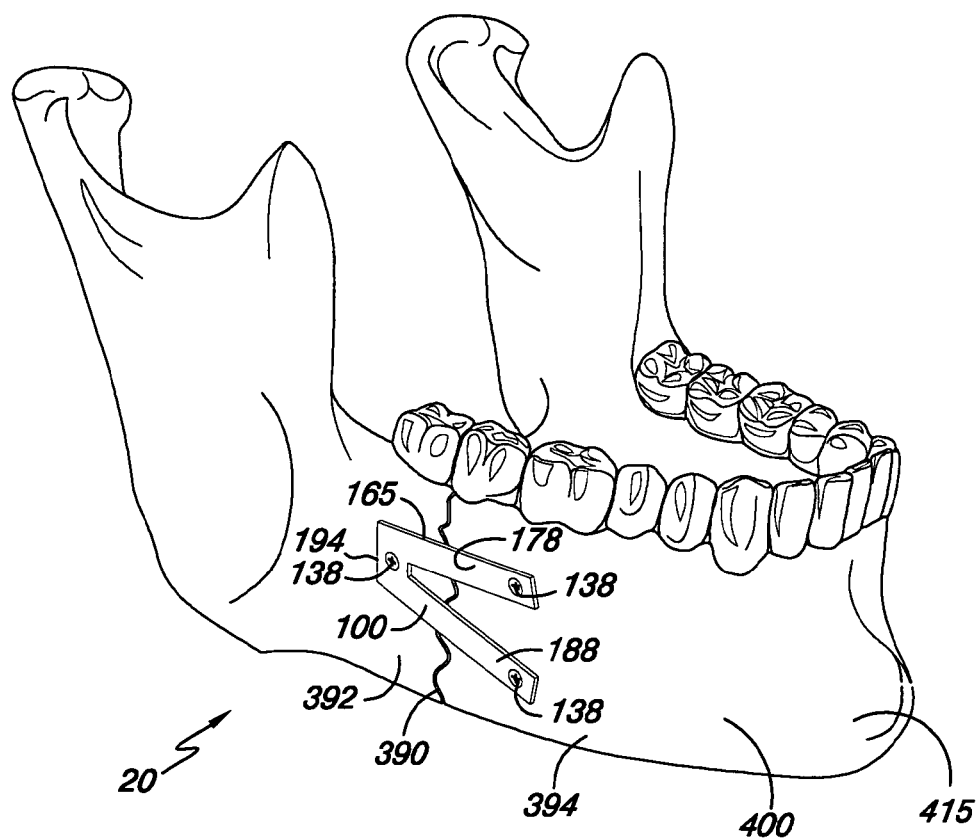
FIG. 1 illustrates a partial perspective view of an exemplary embodiment of a V-shaped bone plate in accordance with the present inventions applied to a fracture of the mandibular bone.

All Figures are illustrated for ease of explanation of the basic teachings of the present invention only; the extensions of the Figures with respect to number, position, relationship and dimensions of the parts to form the embodiment will be explained or will be within the skill of the art after the following description has been read and understood. Further, the exact dimensions and dimensional proportions to conform to specific force, weight, strength, flow and similar requirements will likewise be within the skill of the art after the following description has been read and understood. Where used in various Figures, the same numerals designate the same or similar parts. Furthermore, when the terms "top," "bottom," "right," "left," "forward," "rear," "first," "second," "inside," "outside," and similar terms are used, the terms should be understood to reference only the structure shown in the Figures and utilized only to facilitate describing the illustrated embodiments. Similarly, when the terms "proximal," "distal," and similar positional terms are used, the terms should be understood to reference the structures shown in the Figures as they will typically be utilized by a physician or other user who is treating or examining a patient with an apparatus in accordance with the present invention.

DETAILED DESCRIPTION OF THE INVENTION

The present invention provides an apparatus 20 for the fixation of a bone fracture 390 having a first fracture side 392 and a second fracture side 394. The apparatus includes a bone plate 100 capable of being secured by a plurality of fasteners 138 to a bone surface 400 through a plurality of fastener openings 142. The bone plate 100 is designed to span the bone fracture 390 and to flex in situ so that the bone plate 100 may be fastened to the bone surface 400 on the first fracture side 392 and to the bone surface 400 on the second fracture side 394 of fracture 390 while also providing sufficient stiffness to fixate the fracture 390 by maintaining the fracture 390 in a state of repose.

The thickness h of the bone plate 100 varies over different regions of the bone plate 100 such that there are thick regions 124 and thin regions 125. The thick regions 124 have greater stiffness in a direction perpendicular 199 to a plane 197 of the bone plate 100 than the thin regions 125. The thick regions 124 of the bone plate 100 provide resistance to deflection to maintain fixation of a fracture 390 in the direction perpendicular 199 to the plane 197 of the bone plate. The thin regions 125 of the bone plate 100 allow the bone plate 100 to be compliant in the direction perpendicular 199 to the plane 197 of the bone plate 100 so that the bone plate 100 may flex in conformance with surface curvature and surface irregularities of the bone surface 400. The thin regions 125 may be sufficiently compliant so that the bone plate 100 may flex while positioned in situ. That is, a surgeon may be able to flex the bone plate 100 in accordance with the present invention while the bone plate 100 is positioned on the bone surface 400 while being secured to the bone surface 400. Bending or shaping the bone plate 100 prior to placing the bone plate in situ may not be required. The bone plate 100 is further configured to have stiffness in the plane 197 to maintain fixation of the fracture by resisting forces in the plane and moments. The flexibility of the thin regions 125 of the bone plate 100 increases the ease of surgical attachment of the bone plate 100 to the bone surface 400.

The bone plate 100 may also be configured to function in conjunction with a reduction wire 136 and a reduction wire mount 140 to reduce and fixate the fracture 390. The reduction wire 136 may be a stainless steel wire or any wire or ligature suitable for reduction of the fracture 390. The reduction wire mount 140 may be, without limitation, a bone screw 220, a pin, a post, a nail, or other fastener. The bone plate 100 may include a channel 134 where the channel 134 is configured to receive and slideably retain the reduction wire 136. The channel 136 may be a channel, groove, slot, or the like. The bone plate 100 and reduction wire mount 140 are fastened to opposite sides of the fracture 390 and the reduction wire 136 is attached to the reduction wire mount 140 and received by the channel 134 to extend between the reduction wire mount 140 and the bone plate 100. The bone plate 100, channel 134, reduction wire mount 140, and reduction wire 136 are configured so that placing the reduction wire 136 in tension draws the bone plate 100 and the reduction wire mount 140 toward one another, thereby reducing the fracture 390. Following reduction, the bone plate 100 may then be fastened to the bone surface 400 adjacent the fracture 390. The bone plate is biased against the bone surface 400 by flexing the bone plate 100 in direction perpendicular 199 to the plane 197 and secured to the bone surface 400 so as to fixate the fracture 390.

Method of use of the apparatus 20 according to the present invention may include securing the bone plate 100 to the first fracture side 392, flexing the bone plate 100 in the direction perpendicular 199 to the plane 197 so that the bone plate 100 is biased against the bone surface 400 on the second fracture side 394, and then fixating the fracture 390 by securing the bone plate 100 to the bone surface 400 on the second fracture side 394.

Referring generally to the Figures, the apparatus 20 according to the present invention includes a bone plate 100. The bone plate 100 defines a first surface 130 that is distal to the bone surface 400, and the bone plate 100 defines a second surface 132 that is proximal to the bone surface 400. The first surface 130 is configured to be received against the bone surface 400. The second surface 132 may be configured to be atraumatic, to receive tissue, and to maintain a low profile of the apparatus 20 over the bone surface 400.

A plurality of fastener openings 142 are disposed between the first surface 130 and the second surface 132 so that the bone plate 100 may be secured by a plurality of fasteners 138 to the bone surface 400 through the plurality of fastener openings 142. The fasteners 138 may be bone screws 220, nails, pins, adhesives, or other fasteners recognized by those skilled in the art. The fasteners 138 may be monocortical, bicortical, or combinations thereof. A variety of fasteners 138 may be used in combination. It will be appreciated, however, that the fastener openings 142 would not be present if the bone plate 100 is designed to be secured in other ways such as by various adhesives. The fastener openings 142 may be countersunk 144 so that fasteners 138 are flush with the second surface 132 in order to maintain a low profile of the bone plate 100. The countersinks 144 may be eccentric and oriented to force the bone plate 100 to move parallel to the bone surface 400.

A plane 197 may be defined by the first surface 130 of the bone plate 100. The plane 197 may be flat or may be curvilinear. The plane 197 has a first coordinate direction 201 and a second coordinate direction 203, which may define a rectangular or a curvilinear coordinate system. A perpendicular 199 may be defined with respect to the plane 197.

The geometric configuration of the bone plate 100 depends upon the nature of the fracture 390 that the bone plate 100 is designed to fixate, recognizing that the bone plate 100 must span the fracture 390, must conform to the bone surface 400, and must lend sufficient structural support to the bone surface 400 to maintain fracture 390 fixation. The geometric configuration of the bone plate 100 generally in the plane 197 may be that of a polygon, such as a rectangle, or may be other geometric configurations such as a V-shape 165, an L-shape, or a U-shape. Bone plates 100 having a Y-shape, an H-shape, and irregular shapes in the plane 197 may also be constructed according to the present invention. Thus, it should be appreciated that the shapes in the Figures and otherwise disclosed are merely exemplary and are not a limitation of the shape of the bone plate 100 that may be constructed according to the present invention.

A thickness h may be defined as a distance between the first surface 130 and the second surface 132, the thickness h being measured generally parallel to the perpendicular 199. The general preference is to minimize the thickness h in order to minimize the protrusion of the bone plate 100 above the bone surface 400 to which the bone plate 100 is applied. The bone plate 100 may be of various thicknesses h, and different regions of the bone plate 100 may have different thicknesses h. Thick regions 124 have greater thickness h than thin regions 125.

In a bone plate 100 according to the present invention, the thickness h is arranged to reduce the stiffness of portions of the bone plate 100 in the direction perpendicular 199 to the plane 197 so that the bone plate 100 may flex in the direction perpendicular 199 to the plane 197 in order to conform to the shape of the bone surface 400. The bone plate 100 may flex in situ. The thick regions 124 of the bone plate 100 provide resistance to deflection to maintain fixation of a fracture 390 in the direction perpendicular 199 to the plane 197 of the bone plate 100. The bone plate 100 is further configured to have sufficient stiffness in the plane 197 so as to fixate the fracture 390 by resisting forces and moments in the plane 197 of the bone plate 100. Bone plates 100 having, for example, a V-shape, a Y-shape, or an H-shape have a plurality of arms 232. Said arms 232 may be configured with thin regions 125 and with thick regions h so that each arm 232 may flex in the direction perpendicular 199 to the plane 197. In particular, the arms 232 may flex under the force imparted to the arms 232 by a surgeon when the bone plate 100 is in situ for attachment to the bone surface 400. The arms 232 may be flexed in situ so as to conform to the bone surface 400 and to be secured to the bone surface 400.

An embodiment of an apparatus 20 according to the present invention is illustrated as applied to a fracture 390 of a mandibular bone 415 in FIG. 1. The bone plate 100 is shown as a V-shaped structure 165 in FIG. 1, with a first arm 178 and a second arm 188. The apex 194 of bone plate 100 is secured to a first fracture side 392 of a fracture 390 by a fastener 138 in a fastener 138 in a fastener opening 142. The first arm 178 may be flexed to conform to the shape of the mandibular bone 415 and the second end 182 of the first arm 178 attached to a second fracture side 394. The second arm 188 may be flexed to conform to the shape of the mandibular bone 415 and the second arm 188 attached to the second fracture side 394. The first arm 178 and the second arm 188 may flex under the force imparted to the first arm 178 and to the second arm 188 by a surgeon when the bone plate 100 is in situ. Attachment of the apex 194, the first arm 178 and the second arm 188 fixates the fracture 390 by maintaining the bone fragments in a state of repose.

Although a fracture of the mandibular bone 415 is shown in FIG. 1, it should be understood that an apparatus 20 according to the present invention may be used to reduce and fixate a variety of fractures including a variety of fractures of the various cranial-maxillofacial bones.

Figure 2A:
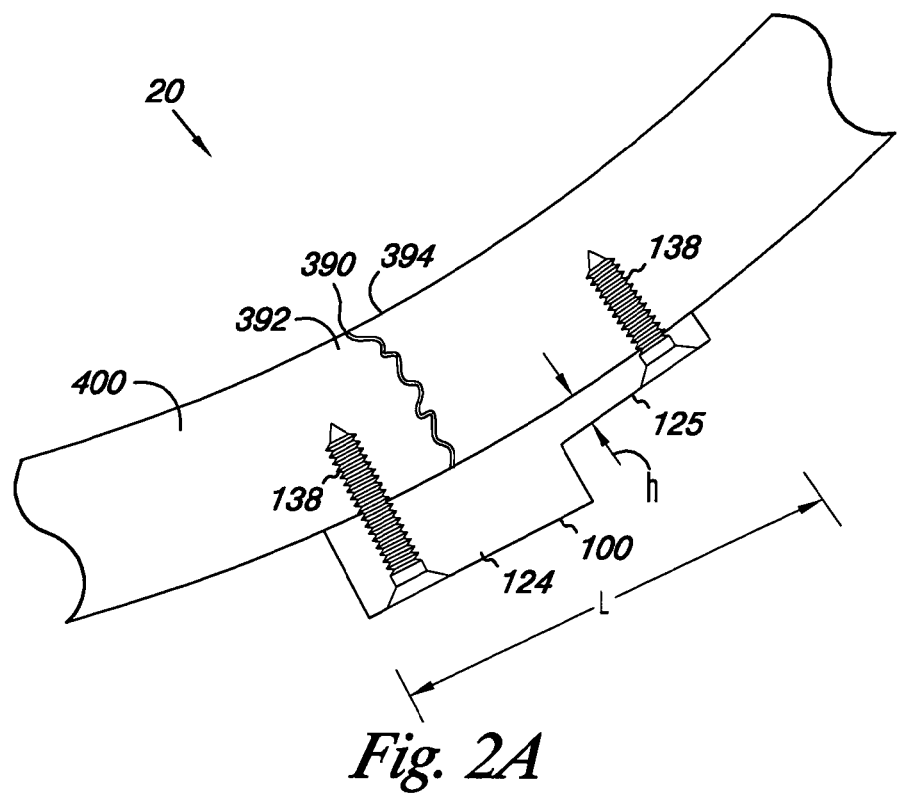
FIG. 2A illustrates a top view of an exemplary embodiment of a bone plate in accordance with the present inventions applied to a bone fracture.
Figure 2B:
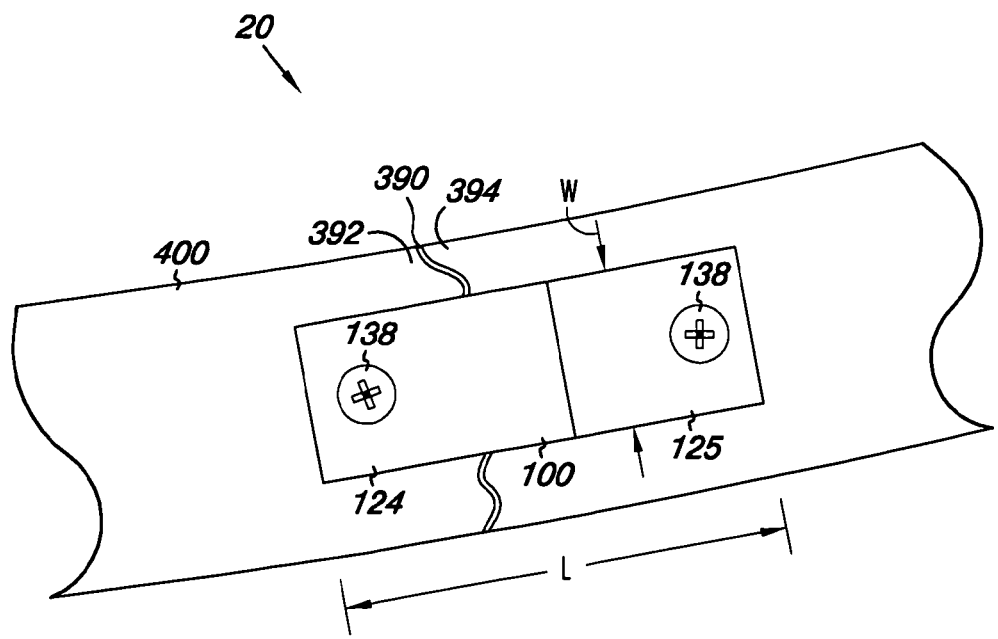
FIG. 2B illustrates a front view of an exemplary embodiment of a bone plate in accordance with the present inventions applied to a bone fracture.

An embodiment of the apparatus 20 according to the present invention is illustrated as applied to a curved bone surface 400 to fixate a fracture 390 in FIGS. 2A and 2B. The apparatus 20 includes a bone plate 100. The bone plate 100 is designed to span a bone fracture surface 400 on a second side 394 of fracture 390 to fixate fracture 390. An apparatus 20 according to the present invention may be used to reduce and fixate a variety of fractures including a variety of fractures of the various cranial-maxillofacial bones including the mandible. In FIGS. 2A and 2B, the bone plate 100 is illustrated as a generally rectangular structure having a thick region 124 and a thin region 125. The bone plate 100, as illustrated, is fastened to a first fracture side 392 by a fastener 138 passing through the thick region 124. The stiffness of the thin region 125 of the bone plate 100 allows the bone plate 100 to flex in situ in conformance to the shape of the bone surface 400 so that the bone plate 100 may be attached to a second fracture side 394 of a fracture 390 by a fastener 138.

Figure 3A:
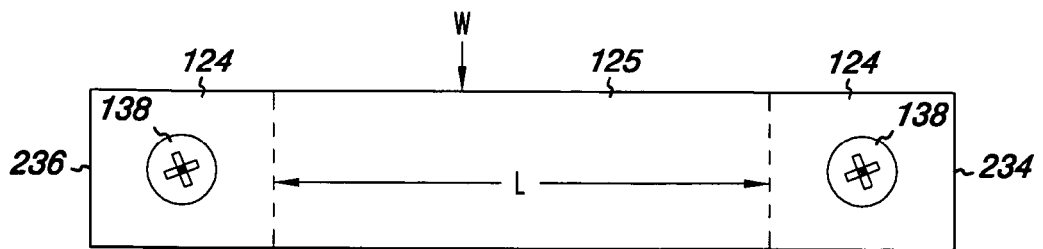
FIG. 3A illustrates a top view of a simplified schematic model of a bone plate in accordance with the present inventions.
Figure 3B:
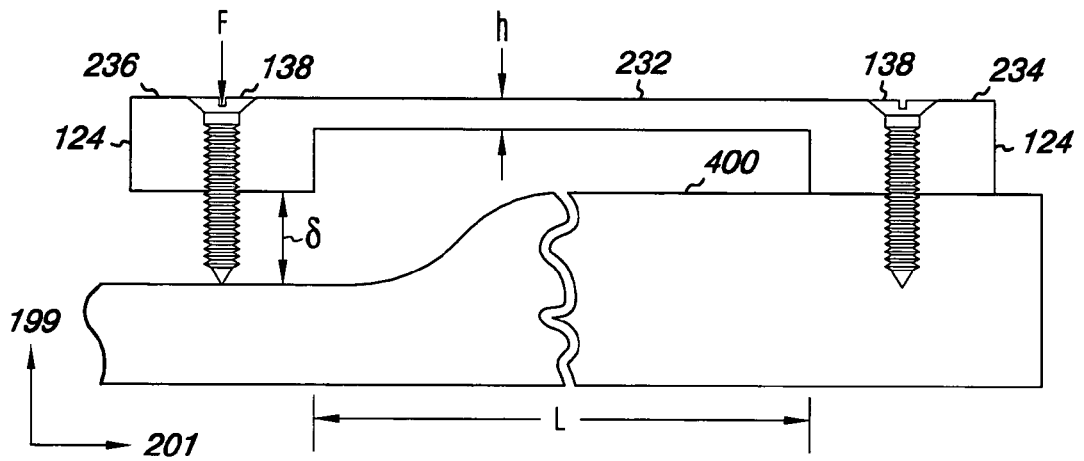
FIG. 3B illustrates a front view of a simplified schematic model of a bone plate in accordance with the present inventions with the bone plate attached to the bone surface on a first fracture side and positioned above the bone surface on a second fracture side.
Figure 3C:
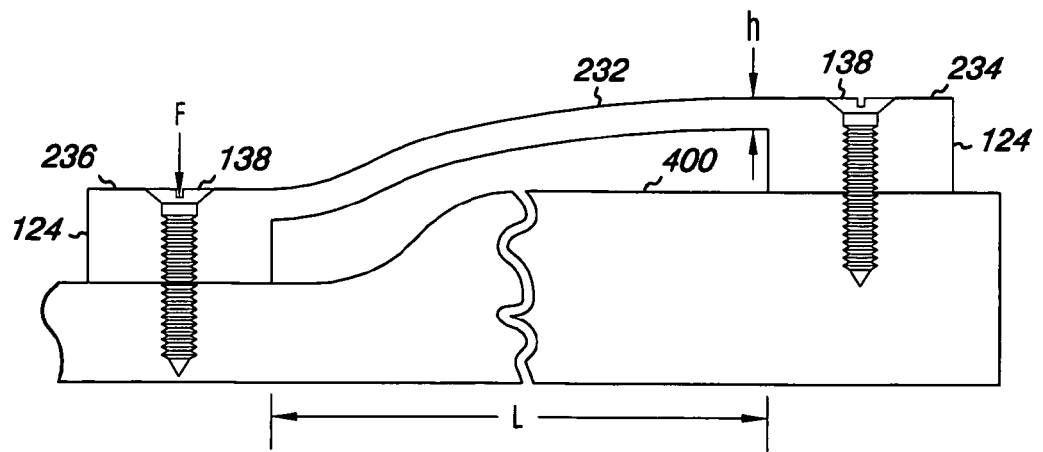
FIG. 3C illustrates a front view of a simplified schematic model of a bone plate in accordance with the present inventions with the bone plate flexed to conform to the bone surface at a fracture.

A simplified schematic model of a bone plate 100 is presented in FIGS. 3A-3C. In FIGS. 3A-3C, the bone plate 100 is illustrated as an arm 232 with a first end 234 and a second end 236. The bone plate 100 has a rectangular shaped thin region 125 of length L extending across the width w of arm 232. The thickness h of the thin region 125 is smaller than the thickness h of the thick regions 124. The thick regions 124 are illustrated as having generally equal thicknesses h, but this is not necessary. The first end 234 is illustrated, in FIG. 3B, as secured to the bone surface 400 by a fastener 138. The second end 236 of the arm 232 may be modeled as a cantilever. The arm 232 may deflect an amount δ in order to conform to the bone surface 400 so that the second end 236 may be secured to the bone surface by a fastener 138, as illustrated in FIG. 3C. The deflection δ of the arm 232 under a force F can be given by:

$$\delta = \frac{4FL^3}{wh^3E} = \frac{1}{K}F \quad (1)$$

where F is the force applied to the second end 236 of the arm 232, w is the width of the arm 232, h is the thickness of the arm 232, L is the length of the arm 232, E is the Young's modulus of elasticity of the material of the arm 232, and K is the stiffness of the arm 232. Some typical values for the Young's modulus for materials commonly used in bone plates 100 including the arm 232 are given in Table I.

TABLE I

| Material | E (Young's Modulus) |
| --- | --- |
| titanium | $1.05 \times 10^{11}$ Pa to $1.20 \times 10^{11}$ Pa |
| steel | $1.90 \times 10^{11}$ Pa to $2.10 \times 10^{11}$ Pa |
| 304 stainless steel | $1.93 \times 10^{11}$ Pa |

A conventional bone plate configured as an arm 232 may have a constant thickness of 1.5 mm throughout its length L including the first end 234 and the second end 236. The embodiment according to the present invention illustrated in FIGS. 3A-3C may have a thickness of 0.20 mm in the thin region 125. Applying equation 1 and assuming that both devices have the same length L, same width w, and are made from the same material, the ratio of the stiffness $K_{conv}$ of the conventional bone plate to the stiffness K of the embodiment of the present invention illustrated in FIGS. 3A-3C in the direction perpendicular 199 to the plane 197 is:

$$\frac{K_{conv}}{K} = 422 \quad (2)$$

A bone plate 100 configured as an arm 232 according to the present invention may have a thin region 125 with a thickness h in the range 0.2 mm≤h≤1 mm. Conventional bone plates 100 may typically have a length L in the range 6 mm≤L≤15 mm and a constant thickness h in the range 1.5 mm≤h≤2 mm throughout.

For example, assuming elastic deformation, an arm 232 according to the present invention made from 304 stainless steel and with L=6 mm, w=2.25 mm and h=0.2 mm in thin region 125 may deflect 1 mm under a force F≈4 N. When a portion of the bone plate 100 has been secured to the bone surface, the surgeon may be able to exert a force F≈4 N to flex the bone plate 100 in situ so that other portions of the bone plate 100 may be secured to the bone surface 400.

By contrast, a conventional bone plate with L=6 mm, w=2.25 mm, and h=1.5 mm would require a force F≈1688 N to deflect 1 mm. A force F≈1688 N could not readily be exerted by the surgeon when the conventional bone plate is in situ.

Figure 4A:
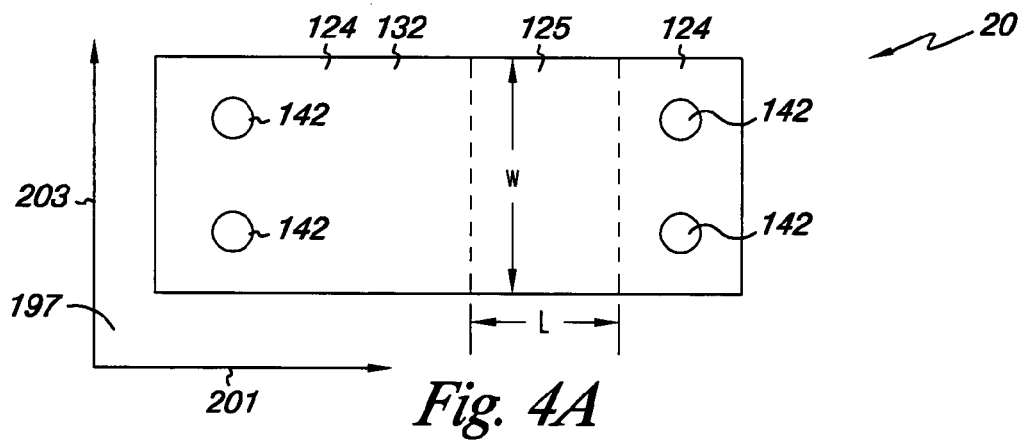
FIG. 4A illustrates a top view of an exemplary embodiment of a bone plate in accordance with the present inventions.
Figure 4B:
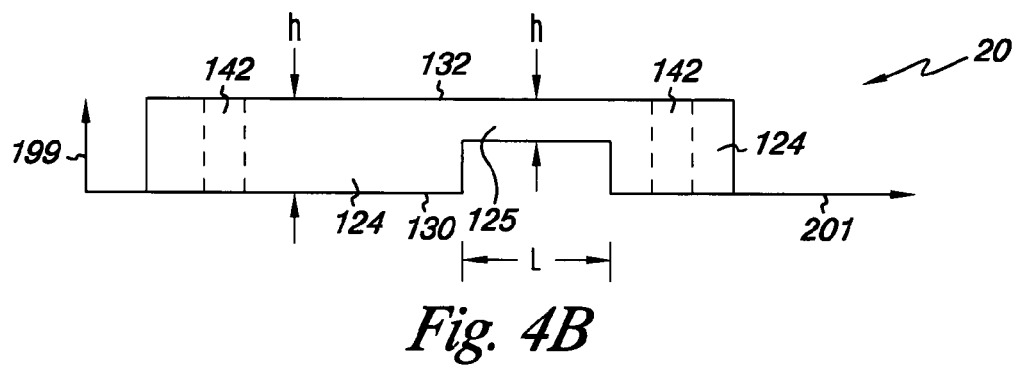
FIG. 4B illustrates a front view of an exemplary embodiment of a bone plate in accordance with the present inventions.

Another embodiment of apparatus 20 according to the present invention is illustrated in FIGS. 4A and 4B. In the embodiment of FIGS. 4A and 4B, the second surface 132 is generally regular and flat. The first surface 130 is configured such that the bone plate 100 has thick regions 124 and a thin region 125. The thin region 125 has a rectangular shape with length L and extends at constant thickness h across the width w of the bone plate 100. The thin region 125 does not necessarily have to assume a rectangular shape nor does the thin region 125 necessarily extend across the width w of the bone plate 100. The thin region 125 reduces the stiffness of the bone plate 100 in the perpendicular 199 so that the bone plate 100 may flex in the perpendicular 199 in situ to be securable, while providing sufficient structural support to resist forces in the plane 197 and also rotation of the plane 197 of the bone plate 100.

Figure 5A:
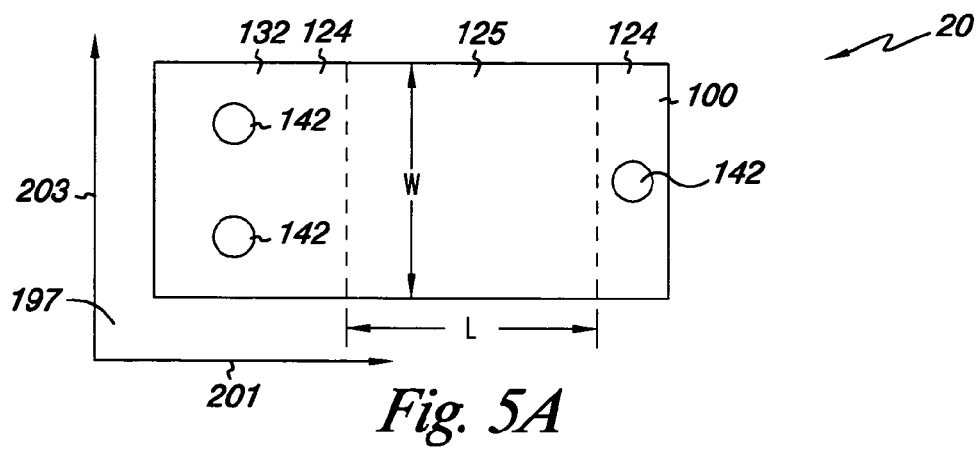
FIG. 5A illustrates a top view of an exemplary embodiment of a bone plate in accordance with the present inventions.
Figure 5B:
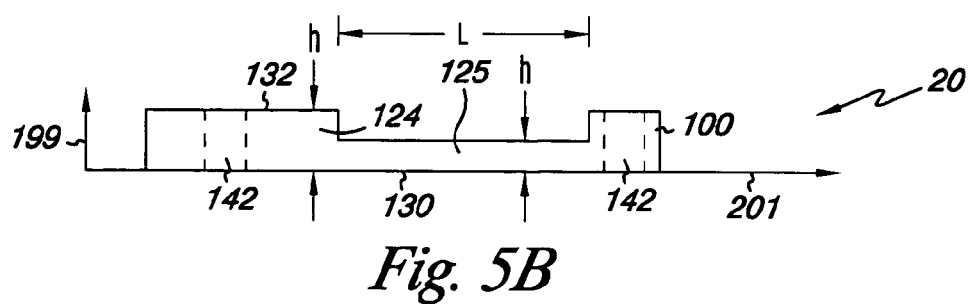
FIG. 5B illustrates a front view of an exemplary embodiment of a bone plate in accordance with the present inventions.

An alternative embodiment of the apparatus 20 according to the present invention is illustrated in FIGS. 5A and 5B. In the embodiment of FIGS. 5A and 5B, the first surface 130, which may be generally biased against the bone surface 400, is generally regular and flat. The second surface 132 is configured such that the bone plate 100 has thick regions 124 and a thin region 125. The thin region 125 has a rectangular shape with length L and the thin region 125 extends across the width w of the bone plate 100. Again, the thin region 125 reduces the stiffness of the bone plate 100 in the perpendicular 199 so that the bone plate 100 may flex in the perpendicular 199 in situ while providing sufficient structural support to resist forces in the plane 197 and also rotation of the plane 197 of the bone plate 100.

Figure 6A:
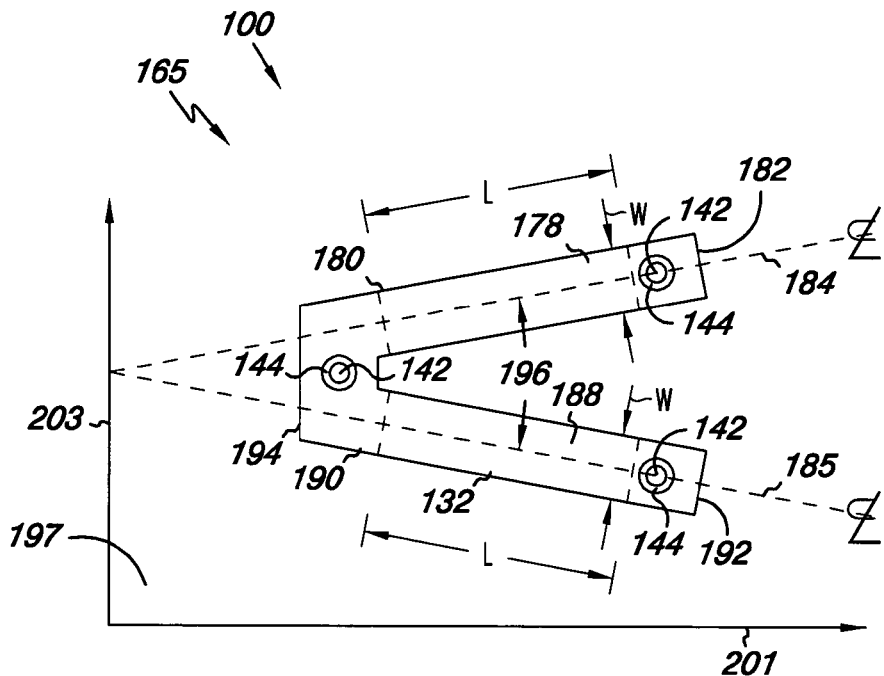
FIG. 6A illustrates a top view of an exemplary embodiment of a bone plate in accordance with the present inventions wherein the bone plate is configured as a V-shaped structure.
Figure 6B:
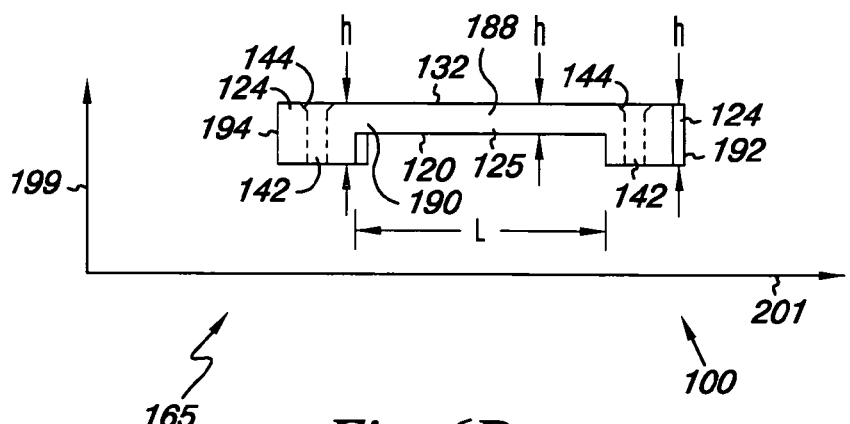
FIG. 6B illustrates a front view of an exemplary embodiment of a bone plate in accordance with the present inventions wherein the bone plate is configured as a V-shaped structure.
Figure 7A:
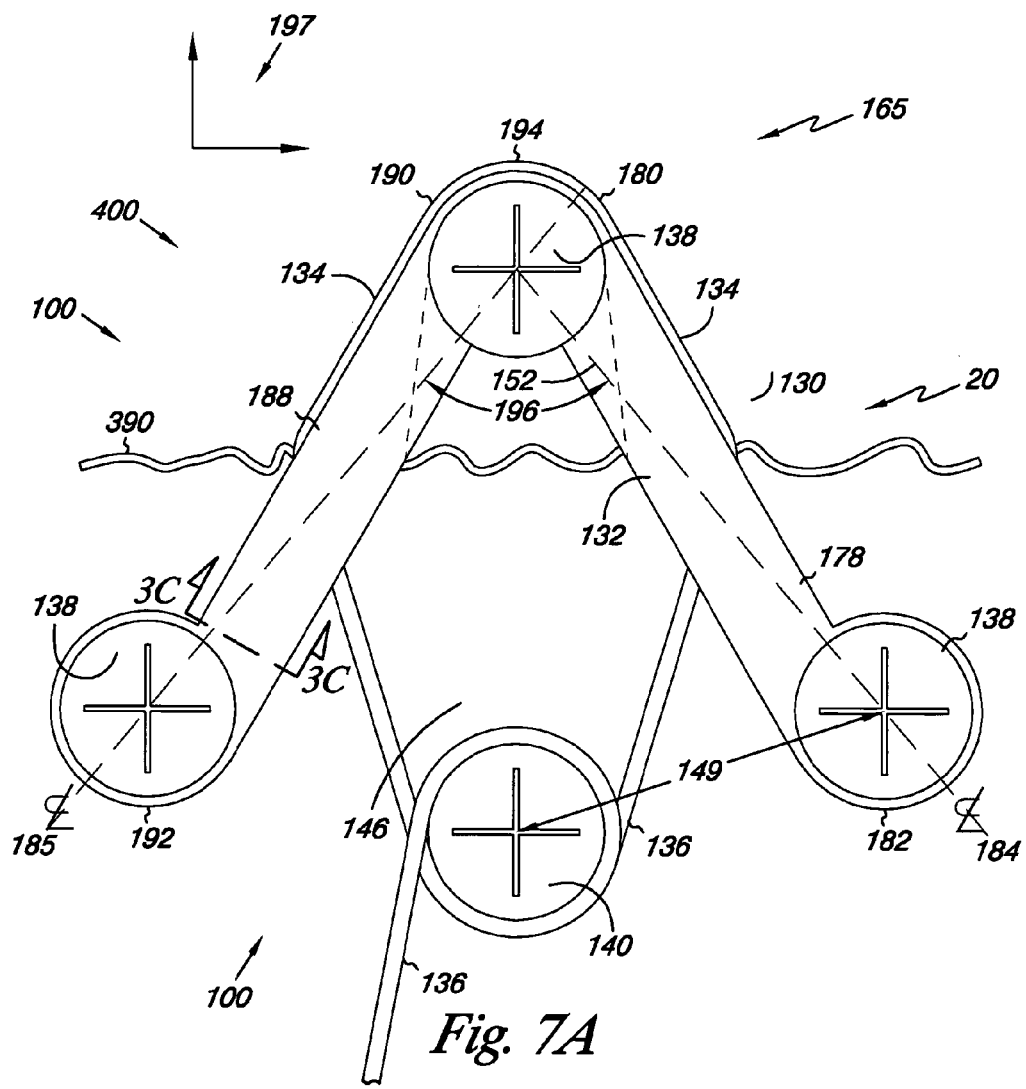
FIG. 7A illustrates a partial proximal perspective view of an exemplary embodiment of an apparatus in accordance with the present inventions wherein the bone plate is configured as a V-shaped structure having a channel, thick regions that support reduction of a fracture, thin regions that provide flexibility, and an apron, and also showing a reduction wire, reduction wire mount, and fasteners.
Figure 7B:
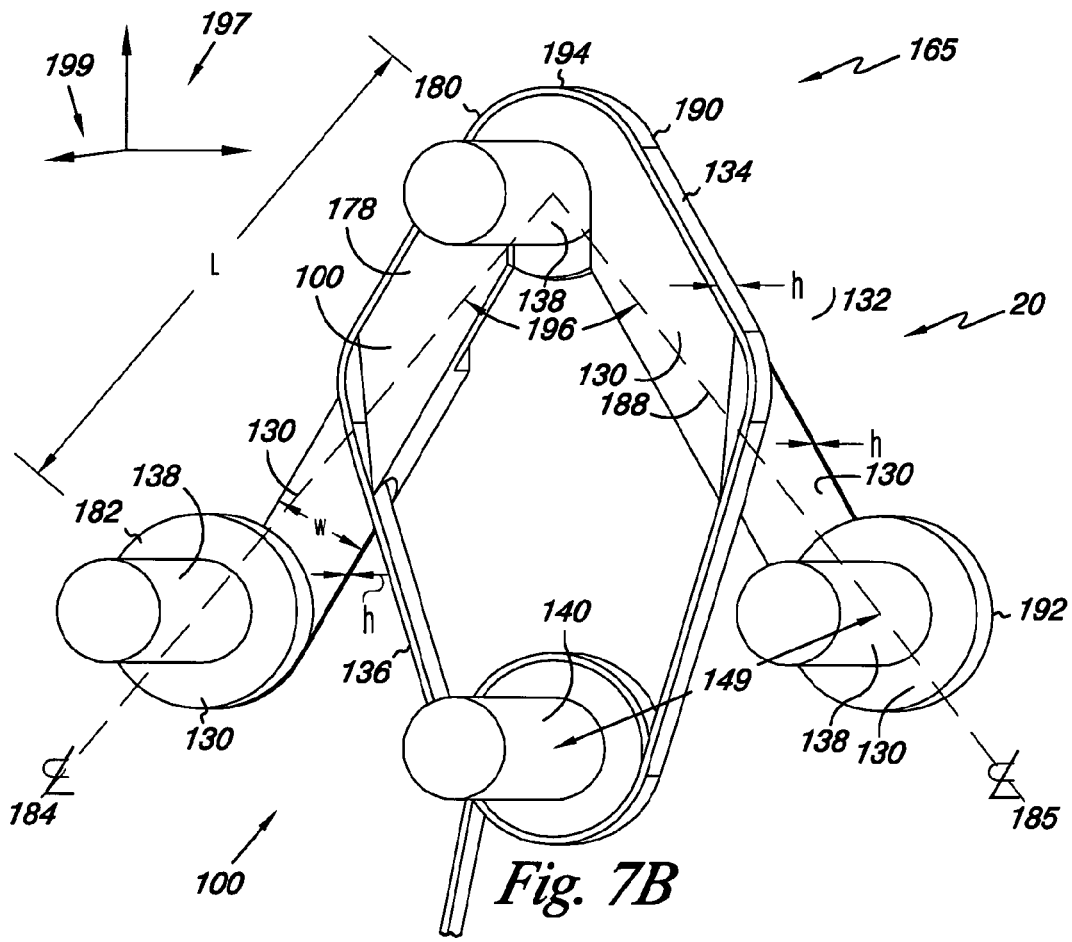
FIG. 7B illustrates a partial distal perspective view of an exemplary embodiment of an apparatus in accordance with the present inventions wherein the bone plate is configured as a V-shaped structure having a channel, thick regions that support reduction of a fracture, thin regions that provide flexibility, and an apron, and also showing the reduction wire, reduction wire mount, and fasteners.
Figure 7C:
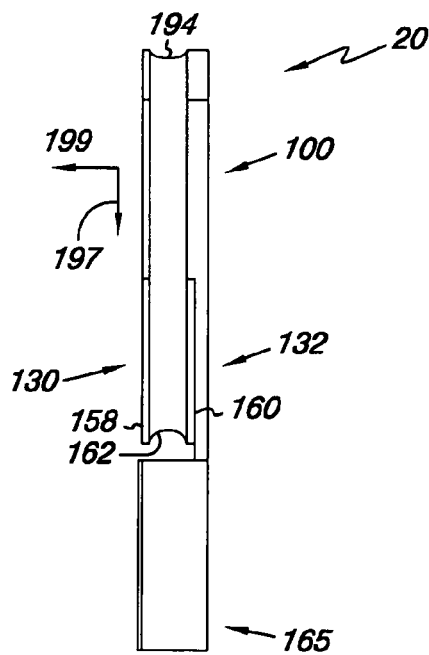
FIG. 7C illustrates a cross-sectional view of an exemplary embodiment of an apparatus in accordance with the present inventions wherein the bone plate is configured as a V-shaped structure having a channel, thick regions that support reduction of a fracture, thin regions that provide flexibility, and an apron.
Figure 7D:
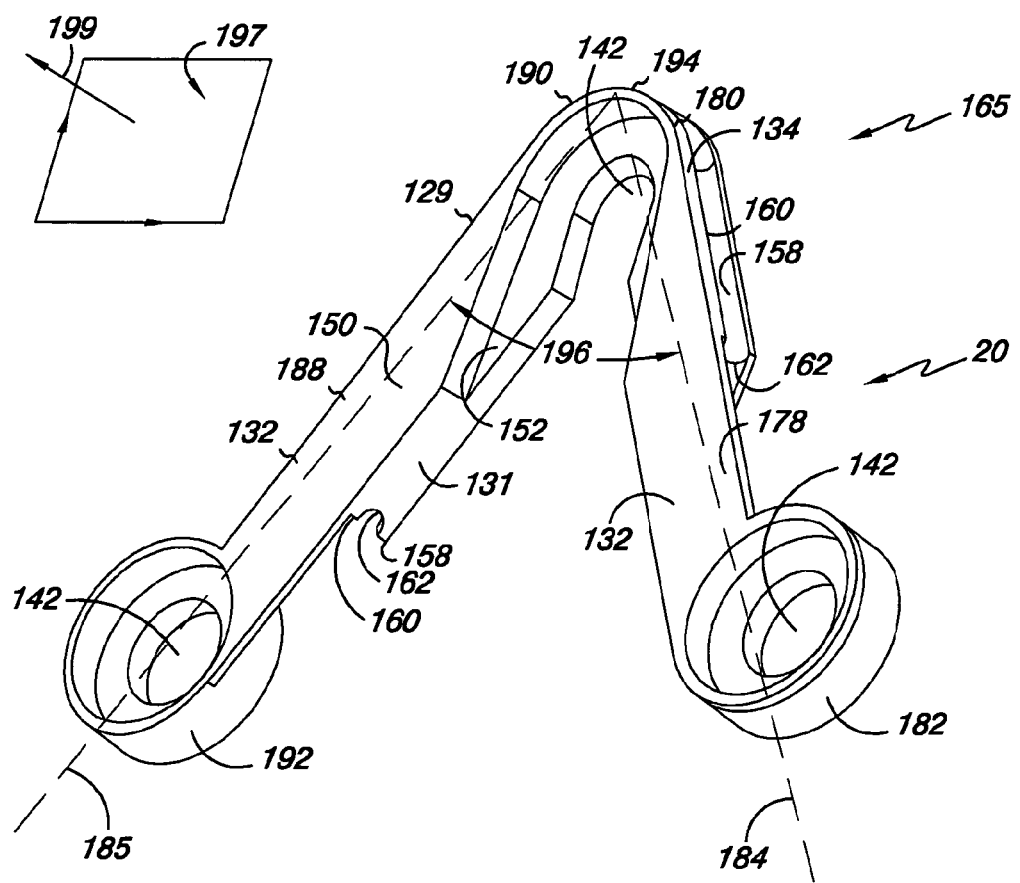
FIG. 7D illustrates a partial proximal perspective view of an exemplary embodiment of an apparatus in accordance with the present inventions wherein the bone plate is configured as a V-shaped structure having a channel, thick regions that support reduction of a fracture, thin regions that provide flexibility, and an apron; and, FIG. 7E illustrates a partial distal perspective view of an exemplary embodiment of an apparatus in accordance with the present inventions wherein the bone plate is configured as a V-shaped structure having a channel, thick regions that support reduction of a fracture, thin regions that provide flexibility, and an apron.
Figure 7E:
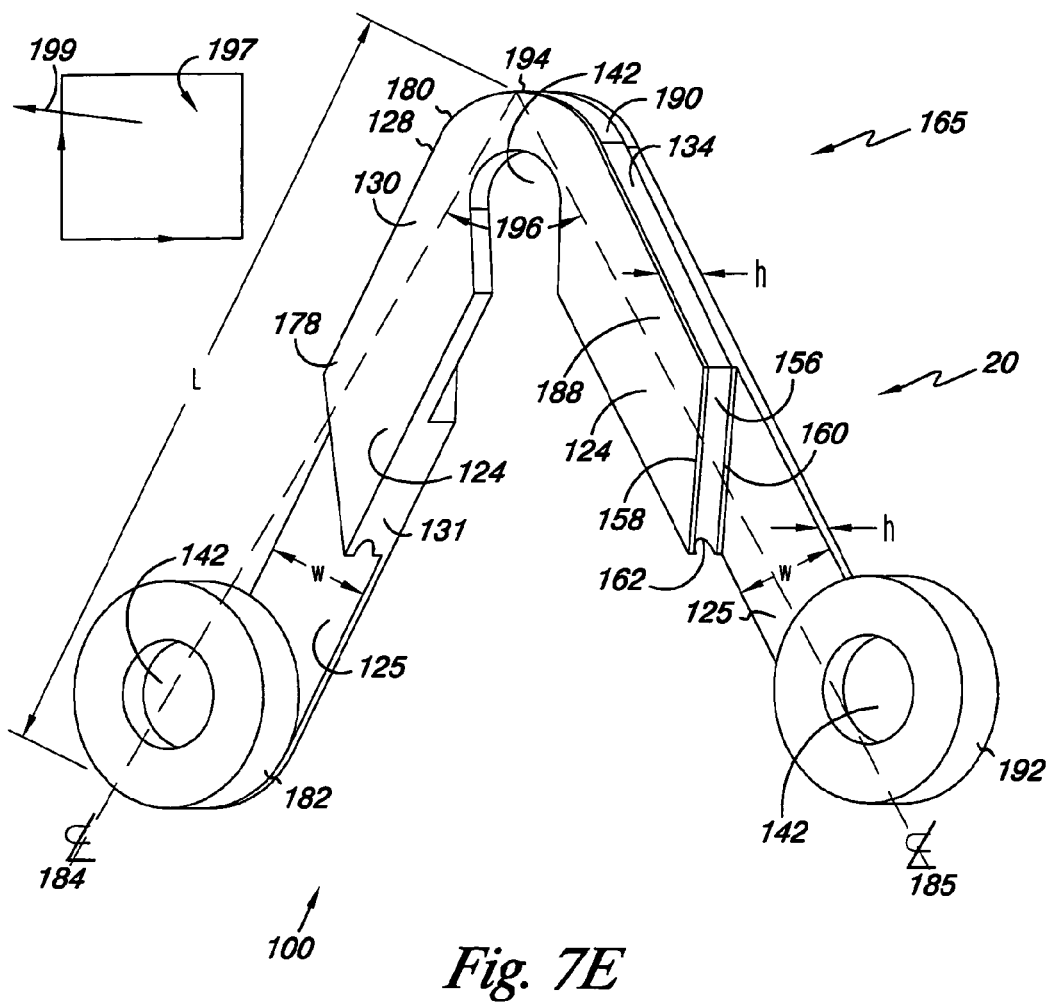

Another embodiment of an apparatus 20 according to the present invention is illustrated in the top view of FIG. 6A and the front view of FIG. 6B. In this embodiment, the bone plate 100 has a generally V-shaped structure 165 with a first arm 178 and a second arm 188. The first arm 178 and the second arm 188 may be approximately the same length, as illustrated, or the first arm 178 and the second arm 188 may be of different lengths. The first arm 178 has a first end 180 and a second end 182, and the second arm 188 has a first end 190 and a second end 192. The bone plate 100 is formed by securing the first end 180 of the first arm 178 to the first end 190 of the second arm 188 thereby forming an apex 194. The first arm 178 has a centerline 184 and the second arm has a centerline 185. The centerline 184 of the first arm 178 intersects the centerline 185 of the second arm 188 so that an angle 196 may be defined between the centerline 184 of the first arm 178 and the centerline 185 of the second arm 188. The distal surface 130 and the proximal surface 132 are shown in the illustration.

The first arm 178 and the second arm 188 may be generally configured to have varying thickness h with respect to the perpendicular 199. In the embodiment illustrated in FIGS. 6A and 6B, the bone plate 100 has a thick region 124 generally proximate the apex 194. The bone plate 100, as illustrated, has a thin region 125 generally along the second arm 188 and a thick region generally proximate the second end 192. The thin region 125 has a rectangular shape with length L and extends across the width w of the second arm 188. In this embodiment, a thin region 125 with length L and extending across the width w of the first arm 178 is also generally disposed along the first arm 178 and a thick region generally proximate the second end 182. The first arm 178 and the second arm 188 may be of equal or varying lengths, and the thin region 125 in the first arm 178 may be configured to be either similar to or different from the thin region 125 in the second arm 188. Even if the first arm 178 and the second arm 188 have substantially the same lengths, the length L of a thin region 125 in the first arm 178 may be different from the length L of a thin region 125 in the second arm 188.

The thin regions 125 in the first arm 178 and in the second arm 188, in the illustrated embodiment, allow the second end 182 of the first arm 178 and the second end 192 of the second arm 188 to flex in situ in the direction perpendicular 199 to the plane 197. Thus, the apex 194 may be secured to a bone surface 400 and the second end 182 of the first arm 178 may be flexed in the perpendicular 199 to the plane 197 such that the second end 182 is biased against the bone surface 400 so that the second end 182 may be secured to the bone surface 400. The second end 192 of the second arm 188 may also be flexed in the perpendicular 199 to the plane 197 such that the second end 192 is biased against the bone surface 400 so that the second end 192 may be secured to the bone surface 400.

The bone plate 100, as illustrated in FIGS. 6A and 6B, may act like an element of a truss in plane 197 so as to resist forces in the plane 197 and resist rotation of the plane 197 of the bone plate 100. Angles 196 of, for example, 45° and 60° are typical for a truss. Examples of stresses in the plane 197 that must be resisted by bone plate 100 would include stresses produced by chewing when the bone plate 100 is fastened to a fractured mandibular bone 415. Further discussion of the stresses may be found in M. B. Trabia, K. G. Zobotkin, and R. C. Wang, *Design of a V-Plate Wire Mandibular Fixation System*, Proc. 2001 ASME Int'l Mech. Eng. Congress, Nov. 11-16, 2001, New York, N.Y., which is hereby incorporated in its entirety by reference.

In the embodiment illustrated by FIGS. 7A-7E, fastener opening 142 are located at the apex 194 and at the second end 182 of the first arm 178 and at the second end 192 of the second arm 188 so that the bone plate 100 may be secured to the bone surface 400 by three fasteners 138. The fastener openings 142, as illustrated in this embodiment, are countersunk 144 in order to maintain a low profile of the bone plate 100 when installed. The bone plate 100 having a V-shaped structure 165 may be variously configured with any suitable number of fastener openings 142 so that any suitable number of fasteners 138 may be used to fasten the bone plate 100 to the bone surface 400. Additionally, the embodiment shown in FIGS. 7A-7E features an apron 152 located proximate the apex 194. The apron 152 is designed to be received under a fastener 138 and to be held by the fastener 138 when the fastener 138 is tightened to engage the apron 152.

The thickness h varies over different regions of the bone plate 100 having a V-shaped structure 165, as illustrated in FIGS. 7A-7E, such that there are thick regions 124 and thin regions 125. The thick regions 124 have greater stiffness in the direction perpendicular 199 to the plane 197 of the bone plate 100 than the thin regions 125. The thick regions 124 of the bone plate 100 provide resistance to deflection to maintain fixation of a fracture 390 in the direction perpendicular 199 to the plane 197 of the bone plate. The thin regions 125 of the bone plate 100 are generally disposed along the first arm 178 and the second arm 188 across the width w of the first arm 178 and the second arm 188 so that the first arm 178 and the second arm 188 are compliant in the direction perpendicular 199 to the plane 197 of the bone plate 100. This allows the first arm 178 and the second arm 188 to flex in situ to surface curvature and surface irregularities of the bone surface 400. The in situ flexibility of the thin regions 125 of the first arm 178 and the second arm 188 in the illustrated embodiment increases the ease of surgical attachment of the bone plate 100 to the bone surface 400.

In the embodiment illustrated in FIGS. 7A-7E, the bone plate 100 has a thick region 124 generally proximate the apex 194. The bone plate 100, as illustrated, has a thin region 125 generally disposed along the first arm 178 and a thick region generally proximate the second end 182. Note that the thin regions 125 are not rectangular but do extend across the width w of the first arm 178 and the second arm 188. In the embodiment of FIGS. 7A-7E, a thin region 125 is also generally disposed along the second arm 188 and a thick region generally proximate the second end 192. The thickness h of the thin region 125 could vary across the width w to have, for example, a greater thickness h along the centerline 184, 185 than adjacent the peripheral surface 131. The thickness h could also vary along the length L of the thin region 125.

The thin regions 125 in the first arm 178 and in the second arm 188, in the illustrated embodiment, allow the second end 182 of the first arm 178 and the second end 192 of the second arm 188 to flex in the direction perpendicular 199 to the plane 197 in situ. Thus, the apex 194 may be secured to a bone surface 400 and the second end 182 of the first arm 178 may be flexed in the direction perpendicular 199 to the plane 197 such that the second end 182 is biased against the bone surface 400 so that the second end 182 may be secured to the bone surface 400. The second end 192 of the second arm 188 may also be flexed in the perpendicular direction 199 to the plane 197 such that the second end 192 is biased against the bone surface 400 so that the second end 192 may be secured to the bone surface 400.

The embodiment illustrated in FIGS. 7A-7E may be used in conjunction with a reduction wire 136 and a reduction wire mount 140 to reduce and fixate a fracture 390. The reduction wire 136 may be a stainless steel wire or any wire or ligature suitable for reduction of the fracture 390. The reduction wire mount 140 may be, for example, a bone screw 220, a pin, a post, a nail, or other fastener known to those skilled in the art.

The embodiment of the bone plate 100 illustrated in FIGS. 7A-7E includes a channel 134 wherein the channel 134 is configured to receive and slideably retain the reduction wire 136. The channel 136 may be a channel, groove, slot, or the like. The bone plate 100, channel 134, reduction wire mount 140, and reduction wire 136 are configured so that placing the reduction wire 136 in tension draws the bone plate 100 and the reduction wire mount 140 toward one another when the bone plate 100 and reduction wire mount 140 are fastened to opposite sides of the fracture 390 and the reduction wire 136 is attached to the reduction wire mount 140 and received by the channel 134 so as to extend between the reduction wire mount 140 and the bone plate 100. Thus, placing the reduction wire 136 in tension draws the first fracture side 392 and the second fracture side 394 together, thereby reducing the fracture 390. Following reduction, the bone plate 100 may then be fastened to both sides of the fracture so as to fixate the fracture.

The channel 134, in the embodiment illustrated in FIGS. 7A-7E, is configured into a portion of a peripheral surface 131 of thick regions 124 of the bone plate 100 generally proximate the apex 194. The channel 134 is illustrated as having a first channel side 158, a second channel side 160, and a channel bottom 162. The first channel side 158 is distal and the second channel side 160 is proximal. The first channel side 158 and the second channel side 160 serve to retain the reduction wire 136 in the channel 134. The channel bottom 162, as illustrated in FIGS. 7A-7E, is curved to bias against the reduction wire 136 to retain the reduction wire 136, while allowing the reduction wire 136 to slide within the channel 134 along the curved channel bottom 162. The reduction wire 136 slides within the channel 134 when a surgeon applies tension to the reduction wire 136, which allows the bone plate 100 and the reduction wire mount 140 to move toward one another so as to bring the fracture 390 into reduction.

The thick region 124 of the bone plate 100 having a V-shaped structure 165, as illustrated in FIGS. 7A-7E, generally proximate the apex 194 should engage the bone on both the first fracture side 392 and the second fracture side 394. This thick region 124 of the bone plate 100, as illustrated in FIGS. 7A-7E, should be sized to have the stiffness necessary to reduce the fracture 390 in the direction perpendicular 199 to the bone plate 100.

The embodiment of the bone plate 100 illustrated in FIGS. 7A-7E may be fastened to the bone surface 400 on a first fracture side 392 of the fracture 390. The bone plate 100 is positioned such that the bone plate 100 will span the fracture 390 in order to be fastened to the second fracture side 394 upon reduction of the fracture 390. The first fracture side 392 for placement of the bone plate 140 and the second fracture side 394 for placement of the reduction wire mount 140 are chosen such that the second fracture side 394 is compressed against the first side 130 of the bone plate 100 when the bone plate 100 is fastened to the bone surface 400 on the first fracture side 392 so that fastening the bone plate 100 to the bone surface 400 on the first fracture side 392 serves to reduce the fracture 390 in the direction perpendicular 199 to the bone plate 100. For example, when the apparatus 20 is used to treat a mandibular fracture, the bone plate 100 is fastened to the buccal-labial (cheek or lip) bone surface 400 of the mandibular bone 415. The side of the fracture 390 having the greater lingual (tongue side) displacement is designated as the first fracture side 392, and the bone plate 100 is fastened to the first fracture side 392. Fastening the bone plate 100 to the first fracture side 392 then forces the second fracture side 394 in the labial direction thereby reducing the buccal-lingual displacement of the fracture 390.

A method of use of the apparatus 20 according to the present inventions may begin by securing the bone plate 100 to the first fracture side 392, then, with the bone plate now in situ, flexing the bone plate 100 in the direction perpendicular 199 to the plane 197 such that the first surface 130 is biased against the bone surface 400 on the second fracture side 394, and finally, securing the bone plate 100 to the bone surface on the second fracture side 394.

Embodiments of bone plate 100 having a V-shaped structure 165 may be used by securing apex 194 to a bone surface 400 on the first fracture side and positioning and orienting the bone plate 100 such that the first arm 178 and the second arm 188 span the fracture 390. The method may continue by flexing the first arm 178 in the direction perpendicular 199 to the plane 197 such that the second end 182 is biased against the bone surface 400, and then securing the second end 182 to the bone surface 400. The next step may be flexing the second end 192 of the second arm 188 in the perpendicular direction 199 to the plane 197 such that the second end 192 is biased against the bone surface 400, and then securing the second end 192 to the bone surface 400.

An embodiment of the apparatus 20 having an apron 152 and a channel 134 for receiving a reduction wire 136 in order to work in conjunction with a reduction wire 136 and reduction wire mount 140, as shown, for example, in FIGS. 7A-7E, is utilized by positioning a fastener 138 on a first fracture side 392 so that a bone plate secured at the apex 194 by the fastener will span the fracture 390 following reduction of the fracture 390, and then securing the fastener 138 to the first fracture side 392. The next step may be orienting the bone plate 100 so that the first surface 130 is distal to the bone surface 400, and then sliding the apron 152 under the fastener 138 so that the apron 152 receives and engages the fastener 138. The method may proceed, if necessary, by tightening the fastener 138 so that the fastener 138 engages the apron 152. Embodiments of the bone plate 100 lacking an apron 152 would be fastened in ordinary ways as recognized by those skilled in the art.

The method continues by mounting a reduction wire mount 140 to the second fracture side 394 of the fracture 390. The reduction wire mount 140 should be properly aligned with respect to the bone plate 100. The reduction wire mount 140 should be located so that the reduction wire 136 will be substantially perpendicular to the fracture 390 when the reduction wire 136 is received by the channel 134 and received by the reduction wire mount 140.

Then, the method may continue by fastening a reduction wire 136 to the reduction wire mount 140 and receiving the reduction wire 136 in the channel 134. The bone plate 100, reduction wire 136, and reduction wire mount 140 should be oriented so that a force applied to the reduction wire 136 will draw the bone plate toward the reduction wire mount 140, and, hence, reduce the fracture 390.

The next step may be reducing the fracture 390 by drawing the first fracture side 392 and the second fracture side 394 of the fracture 390 together by applying tension to the tension wire. Tension is applied to the reduction wire 136 typically by a surgeon 410 pulling on the reduction wire 136

Flexing the first arm 178 in the direction perpendicular 199 to the plane 197 such that the second end 182 is biased against the bone surface 400, and then securing the second end 182 to the bone surface 400 may be the next steps in the method. The method may continue by flexing the second end 192 of the second arm 188 in the perpendicular direction 199 to the plane 197 such that the second end 192 is biased against the bone surface 400, and then securing the second end 192 to the bone surface 400, thereby fixating the fracture 390. Removing the tension wire 136 and removing the tension wire mount 140 may also be included in the method following fixating the fracture 390.

The foregoing discussion discloses and describes merely exemplary embodiments of the present invention, and the dimensions and material properties cited in the foregoing discussion are for exemplary purposes only. It should be understood that no limitation of the scope of the invention is intended thereby. Upon review of the specification, one skilled in the art will readily recognize from such discussion, and from the accompanying drawings and claims, that various changes, modifications and variations can be made therein without departing from the spirit and scope of the inventions as defined in the following claims.

We claim:

1. An apparatus for the fixation of a bone fracture, comprising:
    a bone plate including a first arm and a second arm, wherein the bone plate defines a plane and a perpendicular to the plane, the first arm having a first end and a second end;
    the first and second arms each having one or more thick regions and one or more thin regions, the one or more thick regions and the one or more thin regions disposed about the respective arm so that the respective arm may flex in situ to conform to a bone surface;

the second arm secured by a first end to the first end of the first arm to provide the bone plate with a V-shaped structure;

the bone plate further configured so as to have sufficient stiffness in the plane to support the bone in the plane and to resist out of plane rotation, wherein the thin regions of the first arm are located closer to the second end than the first end; and an apron located at where the first end of the second arm is secured to the first end of the first arm, wherein the apron is configured to be slidably received under a fastener and held by the fastener when the fastener is tightened to engage the apron.

2. The apparatus of claim 1, further comprising a channel, the channel configured to slidably receive a reduction wire.

3. The apparatus of claim 2, wherein the bone plate defines a first surface, the first surface being distal to a bone surface and configured to be biased against the bone surface, the bone plate defines a second surface, the second surface being proximal to the bone surface, and the channel is positioned between at least a portion of the first surface and the second surface.

4. The apparatus of claim 3, wherein the channel is at least partially internally disposed between the first and second surfaces.

* * * * *